United States Patent
Logunov

(10) Patent No.: US 8,895,941 B2
(45) Date of Patent: Nov. 25, 2014

(54) LAMINATED GLASS SHEET DEPTH PROFILE DETERMINATION

(71) Applicant: Stephan Lvovich Logunov, Corning, NY (US)

(72) Inventor: Stephan Lvovich Logunov, Corning, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 13/759,553

(22) Filed: Feb. 5, 2013

(65) Prior Publication Data
US 2013/0221237 A1 Aug. 29, 2013

Related U.S. Application Data

(60) Provisional application No. 61/604,759, filed on Feb. 29, 2012.

(51) Int. Cl.
*G01N 21/64* (2006.01)

(52) U.S. Cl.
CPC .............. *G01N 21/64* (2013.01); *G01N 21/643* (2013.01)
USPC ...................................................... 250/459.1

(58) Field of Classification Search
CPC ............................ G01N 21/64; G01N 21/643
USPC ....................................................... 250/459.1
See application file for complete search history.

(56) References Cited

U.S. PATENT DOCUMENTS

| | | | |
|---|---|---|---|
| 4,323,785 A | 4/1982 | McComb et al. | |
| 4,532,429 A | 7/1985 | Horikawa | |
| 5,457,533 A | 10/1995 | Wilcken | 356/354 |
| 5,498,865 A | 3/1996 | Gaboury et al. | 250/214 |
| 5,604,582 A * | 2/1997 | Rhoads et al. | 356/73 |
| 6,683,695 B1 | 1/2004 | Simpson et al. | |
| 6,962,670 B1 | 11/2005 | Hanson et al. | |
| 7,876,437 B1 | 1/2011 | Furnas et al. | |
| 2004/0099823 A1 | 5/2004 | Abraham et al. | 250/559.4 |
| 2004/0239951 A1 | 12/2004 | Yamanishi et al. | 356/614 |
| 2004/0246493 A1 | 12/2004 | Kim et al. | |
| 2006/0127679 A1 | 6/2006 | Gulati et al. | |
| 2007/0002313 A1 | 1/2007 | Berg et al. | |
| 2008/0050756 A1* | 2/2008 | Paul Kim et al. | 435/7.21 |
| 2011/0205540 A1 | 8/2011 | Moll | |

(Continued)

OTHER PUBLICATIONS

"Measuring Glass Thickness"; DesignNews; http://www.designnews.com/document.asp?doc_id=229015.

(Continued)

*Primary Examiner* — Kiho Kim
(74) *Attorney, Agent, or Firm* — Michael A. Hood; James E. Beyer

(57) ABSTRACT

Depth-sensitive fluorescent spectroscopy can be executed by directing UV radiation through a face of a laminated glass sheet to induce distinct fluorescence in respective target layers of the laminated glass sheet. The respective target layers define glass compositions and relative indices of refraction that permit formation of an externally-viewable fluorescent intensity profile across the target layers of the laminated glass sheet. In an alternative embodiment, non-UV laser radiation is directed from a non-UV laser radiation source through a face of the laminated glass sheet to define a series of multi-photon focal points in the laminated glass sheet and induce fluorescence in respective ones of the plurality of target layers of the laminated glass sheet at a UV excitation frequency that exceeds the frequency of the radiation source.

19 Claims, 1 Drawing Sheet

(56) References Cited

U.S. PATENT DOCUMENTS

| | | | |
|---|---|---|---|
| 2012/0060434 A1* | 3/2012 | Jacobs | 52/173.3 |
| 2012/0068083 A1* | 3/2012 | Labrot et al. | 250/461.1 |
| 2012/0127487 A1* | 5/2012 | Potapenko | 356/632 |
| 2012/0326055 A1* | 12/2012 | Wilson et al. | 250/459.1 |

OTHER PUBLICATIONS

Ineternational Serch Report and Written Opinion issued Apr. 30, 2013 in corresponding PCT application No. PCT/US13/27992, filed Feb. 27, 2013.

* cited by examiner

LAMINATED GLASS SHEET DEPTH PROFILE DETERMINATION

This application claims the benefit of priority under 35 U.S.C. §119 of U.S. Provisional Application Ser. No. 61/604,759 filed on Feb. 29, 2012 the content of which is relied upon and incorporated herein by reference in its entirety.

FIELD

The present disclosure relates to the processing, evaluation, and manufacture of laminated glass sheets.

TECHNICAL BACKGROUND

The processing, evaluation, and manufacture of laminated glass sheets continues to evolve as greater demands are placed upon laminated glass sheets. These demands are typically associated with the development of new uses for laminated glass sheets and with more rigorous demands being placed on glass sheet performance in existing applications.

SUMMARY

The present disclosure is presents methodology for determining the compositional depth profiles of laminated glass sheets by executing depth-sensitive fluorescent spectroscopy. In accordance with one embodiment of the present disclosure, a method of determining a compositional depth profile of a plurality of target layers of a laminated glass sheet is provided. According to the method in some embodiments, depth-sensitive fluorescent spectroscopy is executed by directing UV radiation through a face of the laminated glass sheet into the target layers of the laminated glass sheet to induce distinct fluorescence in respective target layers of the laminated glass sheet, wherein the respective target layers define glass compositions and relative indices of refraction that permit formation of an externally-viewable fluorescent intensity profile across the target layers of the laminated glass sheet. A fluorescence signal detector is positioned to detect image data representing the externally-viewable fluorescent intensity profile; and a fluorescence intensity profile processor is operated to determine a compositional depth profile of the target layers of the laminated glass sheet by generating a depth-sensitive representation of the fluorescent intensity profile across the target layers of the laminated glass sheet.

An imaging camera, for example, may be positioned to detect image data representing the externally-viewable fluorescent intensity profile and an image processor may be operated to determine a compositional depth profile of the target layers of the laminated glass sheet by generating a depth-sensitive representation of the fluorescent intensity profile across the target layers of the laminated glass sheet.

In accordance with another embodiment of the present disclosure, an alternative method is provided where non-UV laser radiation is directed from a non-UV laser radiation source through a face of the laminated glass sheet to define a series of multi-photon focal points in the laminated glass sheet and induce fluorescence in respective ones of the plurality of target layers of the laminated glass sheet at a UV excitation frequency that exceeds the frequency of the radiation source. The respective target layers define glass compositions and relative refractive indices that permit formation of externally detectable fluorescence across the target layers of the laminated glass sheet. A focusing lens is positioned to permit detection of the externally detectable fluorescence across a thickness of the laminated glass sheet and a data processor is operated to determine the compositional depth profile of the target layers of the laminated glass sheet by generating a depth-sensitive representation of the externally detectable fluorescence across the target layers of the laminated glass sheet.

Although the concepts of the present disclosure are described herein with primary reference to three layer glass sheets, it is contemplated that the concepts will enjoy applicability to any glass laminate structure regardless of the number of glass layers forming the structure or the particular profile or geometry of the structure. For example, and not by way of limitation, it is contemplated that the concepts of the present disclosure will enjoy applicability to glass laminate structures that, by design, exhibit non-uniform thickness distributions.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
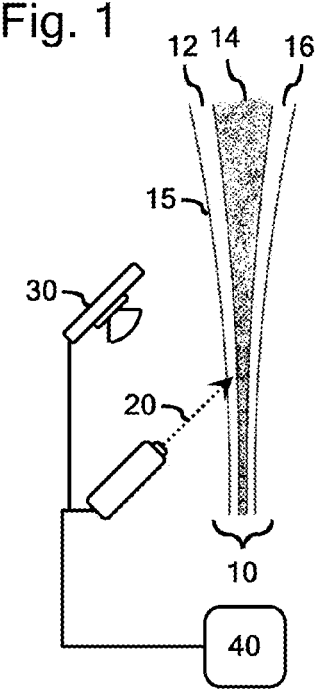
FIG. 1 is a schematic illustration of an off-edge method of determining a compositional depth profile of a laminated glass sheet according to the present disclosure.
Figure 2:
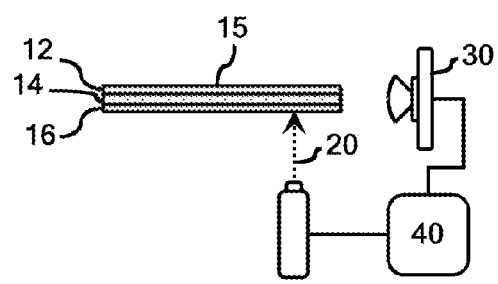
FIG. 2 is a schematic illustration of an on-edge method of determining a compositional depth profile of a laminated glass sheet according to the present disclosure.

Some of the various methods of determining the compositional depth profiles of laminated glass sheets 10 according to the present disclosure are illustrated in FIGS. 1 and 2. In each of these illustrated embodiments, at least two of the target layers 12, 14, 16 of the laminated glass sheet 10 have distinct intrinsic UV-induced fluorescence spectra and the compositional depth profile of the laminated glass sheet 10 is determined by executing depth-sensitive fluorescent spectroscopy. In some embodiments, target layer 14 may be referred to as the core and target layers 12 and 16 may be referred to as the cladding of the laminated glass sheet 10. Optionally, there may be one or more diffusion layers disposed between the core and cladding layers. The target layers are not necessarily distinct layers, for example, each layer may meld into the adjacent layer(s).

According to the illustrated methodology, UV radiation 20 in the form of, for example UV laser radiation 20, UV LED radiation, or some other type of UV light source radiation, is directed through a face 15 of the laminated glass sheet 10 into the target layers 12, 14, 16 of the laminated glass sheet 10 to induce distinct fluorescence in respective target layers 12, 14, 16 of the laminated glass sheet 10. The respective target layers 12, 14, 16 define glass compositions and relative indices of refraction that permit formation of an externally-viewable, fluorescent intensity profile across the target layers 12, 14, 16 of the laminated glass sheet 10. More specifically, the laminated glass sheet 10 can be described as defining a wavelength-dependent absorption window in which between approximately 5% and approximately 85% of the UV radiation 20 is absorbed in the laminated glass sheet 10. The UV radiation 20 falls within this wavelength-dependent absorption window, which may, for example extend from approximately 300 nm to approximately 400 nm.

It is noted that, for the purposes of the present description, the UV-induced fluorescence spectra are "distinct" in the sense that their respective intensities or wavelengths are different enough to be identifiable via available image processing methodology. More specifically, the UV-induced fluorescence of the target layers can be distinct with regard to their respective spectral emission signatures or with regard to their respective intensities.

In some embodiments, one or more imaging cameras 30 are positioned to detect image data representing the externally-viewable fluorescent intensity profile. An image processor 40 is operated to determine a compositional depth profile representing the target layers 12, 14, 16 of the laminated glass sheet 10 by generating a depth-sensitive representation of the fluorescent intensity profile across the target layers 12, 14, 16 of the laminated glass sheet 10. Although the size and shape of the profile will vary depending upon the viewing angle of the imaging camera 30 relative to the laminated glass sheet 10, the UV radiation excitation angle, and the camera magnification, it is contemplated that the image processor 40, the imaging camera 30, or both, can be calibrated to account for the viewing angle, the UV radiation excitation angle, and camera magnification to yield absolute thickness determinations of the target layers 12, 14, 16 of the laminated glass sheet 10. It is contemplated that the image processor 40 may be programmed to execute a spectral deconvolution algorithm to identify target layer transitions and generate the depth-sensitive representation of the sheet 10.

It is also contemplated that the compositional depth profile of the laminated glass sheet 10 can be determined in two-dimensions across the face 15 of the laminated glass sheet 10 to generate a depth profile map of the laminated glass sheet 10. The depth-sensitive representation of the fluorescent intensity profile can be used to determine the compositional depth profile of the laminated glass sheet 10 by comparing the fluorescent intensity profile with pre-existing spectra representing potential target layer compositions. In addition, it is contemplated that the integrated amount of fluorescence from the entire thickness of the laminated glass sheet 10 can be collected through suitable modifications to the image processor 40 and its attendant hardware to provide a depth profile that indicates the thickness uniformity of the entire laminated glass sheet 10 or the individual target layers 12, 14, 16.

In one respect, the methods illustrated in FIGS. 1 and 2 differ with regard to the manner in which the imaging camera 30 is positioned relative to the laminated glass sheet 10. More specifically, FIG. 1 illustrates an "edge-off" configuration where the imaging camera 30 is positioned to detect the intensity profile image data from the perspective of the face 15 of the laminated glass sheet 10. In contrast, FIG. 2 illustrates a laminated glass sheet 10 that a plurality of edge faces extending across the target layers 12, 14, 16 to define respective cross sections of the laminated glass sheet 10. In this "edge-on" embodiment, the imaging camera 30 is positioned to detect the intensity profile image data from the perspective of one of the plurality of edge faces. It is contemplated that the imaging camera may be a visible light imaging camera or any other type of camera suitable for detecting UV-induced fluorescence.

In another respect, the methods illustrated in FIGS. 1 and 2 also differ in the context in which they are used. More specifically, the methodology illustrated in FIG. 2 is particularly applicable to "off-line" processing of finished glass laminate sheets that comprise readily accessible edge faces. In contrast, the methodology illustrated in FIG. 2 is particularly applicable to determining the compositional depth profile of laminated glass sheets "in-line," i.e., during formation of the laminated glass sheet 10, although it could also be utilized for finished glass sheets.

In the "in-line" processing illustrated in FIG. 1, UV radiation 20 can be directed through the face 15 of the laminated glass sheet 10 as the laminated glass sheet 10 is undergoing glass draw processing. The "in-line" methodology of the present disclosure, where UV irradiation can take place before or after the glass sheet 10 is cut to length, further contemplates the use of the determined depth profile as a feedback input to draw processes used in the formation of the laminated glass sheet 10.

Figure 3:
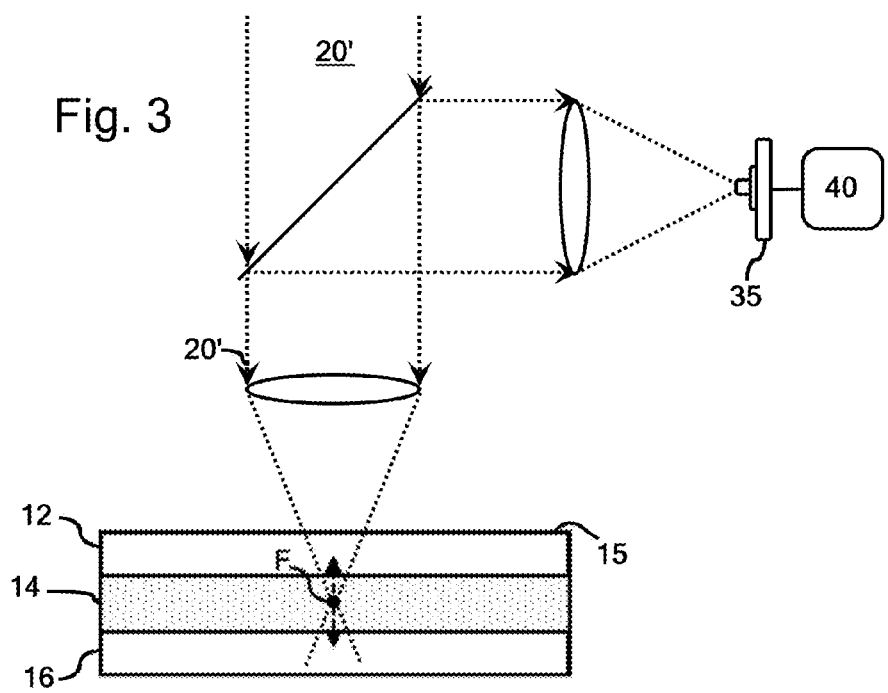
FIG. 3 is a schematic illustration of a multi-photon spectroscopy method of determining a compositional depth profile of a laminated glass sheet according to the present disclosure.

FIG. 3 illustrates alternative methodology that, like the methodology of FIG. 1, is amenable to "in-line," "off-line," "edge-on" or "edge-off" processing. Incident radiation 20' at wavelengths where the glass is substantially transparent, i.e. where no fluorescence can be excited, is directed from a short pulse non-UV source (visible, IR, or near-IR radiation) through a focusing lens 25 and a face 15 of the laminated glass sheet 10 to define a series of multi-photon focal points F in the laminated glass sheet 10. At each of these focal points F the intensity of the pulsed radiation 20' will be sufficient to stimulate multi-photon absorption. More specifically, the laminated glass sheet 10 can be described as defining a wavelength-dependent transmission window, e.g., between approximately 410 nm to approximately 800 nm, or higher, in which at least approximately 90% of the non-UV radiation is transmitted through the laminated glass sheet 10. The non-UV radiation according to this embodiment of the present disclosure falls within this wavelength-dependent transmission window.

A succession of individual multi-photon focal points F can be defined in the laminated glass sheet 10 by altering (i) the focus position of the excitation optics, (ii) the direction of the pulsed focused laser radiation, and/or (iii) a position of the laminated glass sheet 10 relative to the pulsed focused laser radiation. At each of these focal points, the radiation 20' will induce distinct fluorescence in respective ones of the plurality of target layers 12, 14, 16. This distinct fluorescence can be induced at a UV excitation frequency that is approximately twice the frequency of the input radiation source, for two-photon laser excitation, and can be directed to a fluorescence detector 35 via the focusing lens 25 and a beam splitter 32. For excitation beyond two-photon spectroscopy, e.g., three or four-photon processes, the UV excitation frequency will be a higher multiple of the incident radiation, e.g., three times higher for a three-photon process, four times higher for a four-photon process, and so on.

As is the case with the embodiments described with reference to FIGS. 1 and 2, the respective target layers 12, 14, 16 of FIG. 3 define glass compositions and relative indices of refraction that permit formation of distinct externally detectable fluorescence across the target layers 12, 14, 16 of the laminated glass sheet 10. The focusing lens 25 and fluorescence detector 35 can be positioned to detect the externally detectable fluorescence across the target layers 12, 14, 16 of the laminated glass sheet 10 and the image processor 40 can be operated to determine the compositional depth profile of the laminated glass sheet 10 by generating a depth-sensitive representation of the externally detectable fluorescence.

Regardless of the context in which the methodology of the present disclosure is utilized, it is contemplated that the distinct fluorescence in the respective target layers 12, 14, 16 of the laminated glass sheet 10 can be distinct with respect to their respective intensities, frequencies, or both. In addition, it is noteworthy that the distinctions between the distinct fluorescence in respective target layers 12, 14, 16 of the laminated glass sheet 10 need not be attributable to fluorescing additives to the target layers 12, 14, 16 because the target layers 12, 14, 16 of the laminated glass sheet 10, or at least the directly adjacent target layers, commonly have inherently distinct fluorescence spectra.

In practicing the methodology of the present disclosure, it will not be difficult to identify respective target layers 12, 14, 16 compositions and layer thicknesses, e.g., thicknesses less than approximately 1 mm, that permit formation of an externally-viewable fluorescent intensity profile under directed UV radiation of less than approximately 300 mW or, more specifically, between approximately 100 mW and approximately 200 mW. Many suitable target layers 12, 14, 16 will be characterized by respective refractive index differences less than approximately 0.05, and conceivably less than approximately 0.001, at approximately 580 nm and by refractive indices less than approximately 1.55, and conceivably less than approximately 1.48 at 580 nm.

It is contemplated that suitable laminated glass sheets 10 will include, but not be limited to, those comprising an alkali-aluminosilicate cover glass and an aluminosilicate substrate. More generally, it is contemplated that the target layers 12, 14, 16 of the laminated glass sheet 10 can be selected from cover glass compositions, LCD glass compositions, and photovoltaic glass compositions and may comprise glass compositions selected from aluminosilicate, borosilicate, alkali aluminosilicate, etc., and may comprise components selected from rare earth elements, led oxides, iron oxides, zinc oxides, vanadium oxides, arsenic oxides, tin oxides, antimony oxides, germanium oxides, or other fluorescing active oxides, or combinations thereof.

It is noted that recitations herein of a component of the present disclosure being "configured" in a particular way, to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

What is claimed is:

1. A method of determining a compositional depth profile of a plurality of target layers of a laminated glass sheet by executing depth-sensitive fluorescent spectroscopy, wherein at least two of the target layers of the laminated glass sheet have distinct intrinsic UV-induced fluorescence and the method comprises:

directing UV radiation through a face of the laminated glass sheet into the target layers of the laminated glass sheet to induce distinct fluorescence in respective target layers of the laminated glass sheet, wherein the respective target layers define glass compositions and relative indices of refraction that permit formation of an externally-viewable fluorescent intensity profile across the target layers of the laminated glass sheet;

positioning a fluorescence signal detector or an imaging camera to detect image data representing the externally-viewable fluorescent intensity profile; and operating a fluorescence intensity profile processor to determine a compositional depth profile of the target layers of the laminated glass sheet by generating a depth-sensitive representation of the fluorescent intensity profile across the target layers of the laminated glass sheet;

wherein the laminated glass sheet defines a wavelength-dependent absorption window in which between approximately 5% and approximately 85% of the UV radiation is absorbed in the laminated glass sheet, and the UV radiation falls within the wavelength-dependent absorption window.

2. The method of claim 1, wherein:

the laminated glass sheet comprises a plurality of edge faces extending across the target layers to define respective cross sections of the laminated glass sheet; and the imaging camera or the fluorescence signal detector is positioned to detect the fluorescent intensity profile image data from the perspective of one of the plurality of edge faces.

3. The method of claim 1, wherein the imaging camera or the fluorescence signal detector is positioned to detect the intensity profile image data from the perspective of the face of the laminated glass sheet.

4. The method of claim 1, wherein:

the compositional depth profile of the laminated glass sheet is determined during formation of the laminated glass sheet by directing UV radiation through the face of the laminated glass sheet as the laminated glass sheet is undergoing glass draw processing; and the method further comprises utilizing the determined depth profile as a feedback input to draw processes used in the formation of the laminated glass sheet.

5. The method of claim 1, wherein:

the compositional depth profile of the laminated glass sheet is determined during formation of the laminated glass sheet by directing UV radiation through the face of the laminated glass sheet before the glass sheet is cut to length; and the method further comprises utilizing the determined depth profile as a feedback input to draw processes used in the formation of the laminated glass sheet.

6. The method of claim 1, wherein the compositional depth profile of the laminated glass sheet is determined in two-dimensions across the face of the laminated glass sheet to generate a depth profile map or an indication of the thickness uniformity of the laminated glass sheet.

7. The method of claim 1, wherein the fluorescence intensity profile processor, the imaging camera, or fluorescence signal detector, are calibrated to account for a viewing angle of the imaging camera or the fluorescence signal detector relative to the laminated glass sheet, a UV radiation excitation angle, and optical system magnification to yield absolute thickness determinations of the target layers of the laminated glass sheet.

8. The method of claim 1, wherein the fluorescence intensity profile processor is programmed to execute a spectral deconvolution algorithm to identify target layer transitions and generate the depth-sensitive representation of the intensity profile.

9. The method of claim 1, wherein the UV-induced fluorescence of the target layers are distinct with regard to their respective spectral emission signatures, with regard to their respective intensities of UV-induced fluorescence, or both.

10. The method of claim 1, wherein distinctions between the distinct fluorescence in respective target layers of the laminated glass sheet are not attributable to fluorescing additives to the target layers.

11. The method of claim 1, wherein the depth-sensitive representation of the fluorescent intensity profile is used to determine the compositional depth profile of the laminated glass sheet by comparing the fluorescent intensity profile with pre-existing spectra representing potential target layer compositions.

12. The method of claim 1, wherein the respective target layers define glass compositions and layer thicknesses that permit formation of an externally-viewable fluorescent intensity profile across the target layers of the laminated glass sheet under directed UV radiation of less than approximately 300 mW.

13. The method of claim 1, wherein the target layers of the laminated glass sheet are characterized by respective refractive index differences less than approximately 0.05.

14. The method of claim 1, wherein the target layers of the laminated glass sheet are characterized by refractive indices less than approximately 1.55.

15. The method of claim 1, wherein the target layers of the laminated glass sheet comprise an alkali-aluminosilicate cover glass and an aluminosilicate substrate.

16. The method of claim 1, wherein the target layers of the laminated glass sheet are selected from cover glass compositions, LCD glass compositions, and photovoltaic glass compositions and comprise components selected from tin oxides, antimony oxides, rare earth elements, led oxides, iron oxides, zinc oxides, vanadium oxides, arsenic oxides, tin oxides, antimony oxides, germanium oxides, or other fluorescing active oxides, or combinations thereof.

17. The method of claim 1, wherein the target layers of the laminated glass sheet comprise glass compositions selected from aluminosilicate, borosilicate, or alkali aluminosilicate, glass compositions.

18. A method of determining a compositional depth profile of a plurality of target layers of a laminated glass sheet by executing depth-sensitive fluorescent spectroscopy, wherein at least two of the target layers of the laminated glass sheet have distinct intrinsic UV-induced fluorescence and the method comprises:
  directing non-UV laser radiation from a non-UV laser radiation source through a face of the laminated glass sheet to define a series of multi-photon focal points in the laminated glass sheet and induce fluorescence in respective ones of the plurality of target layers of the laminated glass sheet at a UV excitation frequency that exceeds the frequency of the radiation source, wherein the respective target layers define glass compositions and relative refractive indices that permit formation of externally detectable fluorescence across the target layers of the laminated glass sheet;
  positioning a focusing lens to permit detection of the externally detectable fluorescence across a thickness of the laminated glass sheet; and
  operating a data processor to determine a compositional depth profile of the target layers of the laminated glass sheet by generating a depth-sensitive representation of the externally detectable fluorescence across the target layers of the laminated glass sheet;
  wherein the laminated glass sheet defines a wavelength-dependent transmission window in which at least approximately 90% of the non-UV radiation is transmitted through the laminated glass sheet, and the non-UV radiation falls within the wavelength-dependent transmission window.

19. A method of determining a compositional depth profile of a plurality of target layers of a laminated glass sheet by executing depth-sensitive fluorescent spectroscopy, wherein at least two of the target layers of the laminated glass sheet have distinct intrinsic UV-induced fluorescence and the method comprises:
  directing UV radiation through a face of the laminated glass sheet into the target layers of the laminated glass sheet to induce distinct fluorescence in respective target layers of the laminated glass sheet, wherein the respective target layers define glass compositions and relative indices of refraction that permit formation of an externally-viewable fluorescent intensity profile across the target layers of the laminated glass sheet;
  positioning a fluorescence signal detector or an imaging camera to detect image data representing the externally-viewable fluorescent intensity profile; and
  operating a fluorescence intensity profile processor to determine a compositional depth profile of the target layers of the laminated glass sheet by generating a depth-sensitive representation of the fluorescent intensity profile across the target layers of the laminated glass sheet;
  wherein the target layers of the laminated glass sheet are selected from cover glass compositions, LCD glass compositions, and photovoltaic glass compositions and comprise components selected from tin oxides, antimony oxides, rare earth elements, lead oxides, iron oxides, zinc oxides, vanadium oxides, arsenic oxides, germanium oxides, other fluorescing active oxides, or combinations thereof.

* * * * *